(12) United States Patent
Svanbäck et al.

(10) Patent No.: US 11,131,658 B2
(45) Date of Patent: Sep. 28, 2021

(54) METHOD AND DEVICE FOR PHYSICOCHEMICAL CHARACTERIZATION OF MATERIALS

(71) Applicant: University Of Helsinki, Helsingin Yliopisto (FI)

(72) Inventors: Sami Svanbäck, Helsinki (FI); Jouko Yliruusi, Vantaa (FI); Henrik Ehlers, Espoo (FI); Osmo Antikainen, Helsinki (FI); Heikki Räikkönen, Helsinki (FI)

(73) Assignee: The Solubility Company Oy, Helsinki (FI)

( * ) Notice: Subject to any disclaimer, the term of this patent is extended or adjusted under 35 U.S.C. 154(b) by 232 days.

(21) Appl. No.: 16/096,936

(22) PCT Filed: Apr. 28, 2017

(86) PCT No.: PCT/FI2017/050328
§ 371 (c)(1),
(2) Date: Oct. 26, 2018

(87) PCT Pub. No.: WO2017/187023
PCT Pub. Date: Nov. 2, 2017

(65) Prior Publication Data
US 2019/0094197 A1    Mar. 28, 2019

(30) Foreign Application Priority Data

Apr. 29, 2016 (FI) .................................... 20165372

(51) Int. Cl.
*G01N 33/15* (2006.01)
*G01N 13/00* (2006.01)

(52) U.S. Cl.
CPC ............ *G01N 33/15* (2013.01); *G01N 13/00* (2013.01); *G01N 2013/006* (2013.01)

(58) Field of Classification Search
CPC .. G01N 13/00; G01N 2013/006; G01N 33/15; G01N 15/02; G01N 21/85
USPC ......... 436/34, 164, 174, 180; 422/82.05, 547
See application file for complete search history.

(56) References Cited

U.S. PATENT DOCUMENTS

| | | | |
|---|---|---|---|
| 4,279,860 A | 7/1981 | Smolen | |
| 6,929,782 B1* | 8/2005 | Ciliberto | B01L 3/508 422/561 |
| 8,119,998 B2* | 2/2012 | Avdeef | G01N 21/82 250/461.1 |
| 2004/0151360 A1 | 8/2004 | Pirard et al. | |

(Continued)

FOREIGN PATENT DOCUMENTS

| CN | 101398354 A | 4/2009 |
|---|---|---|
| CN | 101461033 A | 6/2009 |

(Continued)

OTHER PUBLICATIONS

Svanback et al. Analytical Chemistry, vol. 87, pp. 5041-5045, Apr. 27, 2015.*

(Continued)

*Primary Examiner* — Maureen Wallenhorst
(74) *Attorney, Agent, or Firm* — Ziegler IP Law Group, LLC (57) ABSTRACT

An analysis method and device including detecting at least one particle of matter in a fluid inside in a reaction chamber and correlating a change in the particle to a physicochemical property of the matter.

12 Claims, 3 Drawing Sheets

(56) References Cited

U.S. PATENT DOCUMENTS

| | | | |
|---|---|---|---|
| 2009/0064768 A1* | 3/2009 | Alkhawam | G01N 13/00 |
| | | | 73/64.56 |
| 2012/0034704 A1 | 2/2012 | Hughes et al. | |
| 2018/0231446 A1* | 8/2018 | Svanback | G01N 13/02 |
| 2019/0204286 A1* | 7/2019 | Pessi | G01N 33/15 |

FOREIGN PATENT DOCUMENTS

| | | |
|---|---|---|
| CN | 101558289 A | 10/2009 |
| CN | 102301221 A | 12/2011 |
| CN | 104662407 A | 5/2015 |
| CN | 105308715 A | 2/2016 |
| EP | 0578630 A1 | 1/1994 |
| JP | 2005521425 A | 7/2005 |
| WO | 03085379 A2 | 10/2003 |
| WO | 2008153493 A1 | 12/2008 |
| WO | 2016030583 A1 | 3/2016 |

OTHER PUBLICATIONS

Written opinion of the international search authority, Application No. PCT/FI2017/050328, dated Oct. 5, 2017.
International Search Report, Application No. PCT/FI2017/050328, dated Oct. 5, 2017, 9 pages.
Svanback, Sami et al.Optical microscopy as a comparitive analytical technique for single particle dissolution studies, International Journal of Pharmaceutics, vol. 469, 2014 pp. 10-16.
Finnish Patent and Registration Office, Search Report, Application No. 20165372, dated Nov. 29, 2016, 2 pages.
The Patent Office of the People's Republic of China, Notification of the First Office Action, Application No. 2017800265610, dated Feb. 19, 2021, 7 pages.
The State Intellectual Property Office of People's Republic of China, Search Report, Application No. 2017800265610, dated Feb. 4, 2021, 3 pages.
Japan Patent Office, Notification of ground of rejection, Application No. 2018-555575, dated May 10, 2021, 8 pages.

* cited by examiner

METHOD AND DEVICE FOR PHYSICOCHEMICAL CHARACTERIZATION OF MATERIALS

FIELD

The present aspects of the disclosed embodiments generally relate to physicochemical characterization of matter.

BACKGROUND

High-content analysis (HCA), based on automated image analysis, has become a widely used and valuable technique in biosciences.

In particular, two physicochemical properties of materials determine their fate in different chemical environments, namely solubility and lipophilicity. The solubility of a compound determines the extent to which the compound will be present in its molecular active form, thus determining for example the bioavailability and the extent of therapeutic or toxic effects the compound will exhibit. Solubility also plays an important role in for example nucleation processes, being of high relevance in synthesis and crystallization.

The partition/distribution coefficient (log P/log D) describes the lipophilic nature of the compound, determining the partition in e.g. the environment and the human body. The pH independent partition coefficient (P) or the pH dependent distribution coefficient (D) is the most used physicochemical parameters to estimate permeation through biological membranes and absorption phenomena. log P and log D have also been shown to be a good predictors of environmental fate and toxicity of compounds in both natural environments as well as on a cellular level.

Current standard techniques to determine the above physicochemical parameters usually take several hours or even days. Quantification methods are commonly based on substance specific and solvent specific chemical analysis, requiring further development time and resources. Another significant drawback of standard methods, besides the long experimental times, is high use of analytes and reagents, which increases cost and environmental impact. Computational models are also used to estimate these physicochemical factors, but they require experimental input parameters for accurate predictions. Moreover, experimental input parameters have to be acquired under a range of relevant experimental conditions reflecting the model environment, which may make their application impractical.

Current particle characterization devices determine average particle sizes or particle size distributions. In applications where individual particles are characterized, the particles are fixed by gluing, clamping or by other mechanical means. Individual particles can also be hydrodynamically positioned, or positioned by acoustic or optic means, for continuous imaging. Mechanical affixation is laborious and potentially alters particle properties. Positioning, on the other hand, is often challenging and temporary, especially for small particles.

Accordingly, it is an aim of the present disclosure to alleviate at least some of the above problems.

It is another aim to provide a simple and low-cost method and apparatus for determining physicochemical properties of matter or particle(s).

SUMMARY

According to a first aspect there is provided a characterization method, comprising:
i. Providing at least one particle on a surface
ii. Providing at least one fluid
iii. Allowing the fluid to come into contact with the particle(s)
iv. Detecting the particle(s)
v. Analyzing from data acquired during the detecting changes in the particle(s); and
vi. Correlating the changes to a physicochemical property of the material of the particle(s).

According to another aspect there is provided a characterization method, comprising:
i. Providing at least one particle on a surface
ii. Providing at least one fluid
iii. Allowing the fluid to come into contact with the particle(s)
iv. Detecting the particle(s)
v. Analyzing from data acquired during the detecting changes in the particle(s); and
vi. Correlating the changes to at least one physicochemical property of the fluid.

In certain embodiments detecting comprises detecting no change between two data points.

As the fluid contacts the particle(s) e.g. by providing the particle(s) in a fluid stream inside a reaction chamber, the fluid stream may dissolve the particle(s) while the concentration profile around the individual particle(s) changes or remains unchanged. This may result into a rate of dissolution and, consequently, in a decrease in particle(s) size, which can be detected e.g. imaged through e.g. a transparent window in the reaction chamber. Analysis can be automated to extract individual particle(s) data as a function of time from the acquired data.

The method is advantageous in allowing measuring various physicochemical properties of the detected, e.g. imaged particle(s), or the fluid. Depending on the particle(s), the physicochemical property is to be selected as desired. The method is useful e.g. for measuring changes in the particle(s) when exposed to a different chemical and/or physical environments, such as temperature, radiation, pressure, ionic strength, pH, or a biologically active agent.

The method may also be useful for analyzing particle(s) having a mass more than three orders of magnitude less than what is required in current state of the art miniaturized methods. The performance of the present method is much better than what can be achieved with standard methods, which operate in the mg and g range. For example, the method can be used to acquire a solubility-lipophilicity-charge state profile of compounds in nanogram scale. As evidence by examples provided below, an average change in mass between two subsequent detection points, can be detected in picogram scale, or even femtogram scale, using a real-time detection in less than a minute. Thus, the detection limit of the method may be on the similar level as that of current advanced analytical methods, such as mass spectrometry. The solubility in a specific chemical or physical environment can in an embodiment be determined with adequate accuracy from the slope of the decreasing particle area and/or radius and/or other changing property of the imaged particle(s) as the only required parameter. This allows e.g. fast and complete physicochemical characterization of an unknown substance of unknown chemical and physical composition. The simple and cost-effective setup, and the wide applicability using e.g. conventional optical microscopy, gives a substantial advantage to this technique.

An ability to screen physicochemical properties across a wide range of chemical environments is of great value in many fields. Without limiting to any particular advantage, with the present method it is possible to achieve in a rapid, efficient, robust and cost-effective manner at least nine fundamental physicochemical properties of matter: dissolution rate, intrinsic dissolution rate (IDR), native solubility, intrinsic solubility, equilibrium solubility, apparent solubility, pKa, log P, and log D. These parameters can be determined even from individual nanogram crystals using automated data analysis. Automated detecting based analysis of nanogram amounts of substance, without liquid sampling or sample treatment or handling steps, substantially reduces consumption and potentially toxic waste. In addition, operator contact with potentially hazardous substances is substantially reduced. It also allows for compounds of high value or scarce availability, such as in drug development, to be reliably analyzed.

In an embodiment the characterization method according to the first aspect comprises a further step vii. comprising correlating the changes to at least one physicochemical property of the fluid. This embodiment is advantageous in that it can be used to simultaneously characterize the material of the particle, and the fluid.

The characterization method can be used to characterize at least one physicochemical property of the fluid. In an embodiment the changes in the particle can be correlated either with at least one physicochemical property of the material of the particle, or the fluid, such as capability of the fluid to dissolve the material of the particle.

In embodiment the fluid comprises a suspension vehicle. In a further embodiment the suspension vehicle is used to screen in vivo formulations.

Without limiting to any particular affixation technique, with the present method it is possible to immobilize one or several particles on a surface of a detection area, allowing detection of specific particle(s). Immobilization towards a permeable/semipermeable layer allows for particle(s) to be prepositioned or be supplied manually or automatically by mechanical means or with a fluid flow across and/or through the layer.

According to a second aspect is provided an analysis device comprising

A reaction chamber;

At least one first inlet for passing a fluid into the reaction chamber;

At least one outlet for passing fluid outside the reaction chamber;

An immobilization zone arranged inside the reaction chamber configured to allow immobilizing particles in a fluid; and Means allowing detecting the immobilization zone.

According to a third aspect is provided a system comprising the analysis device of the second aspect, and further comprising fluid handling means for controlled passing of the fluid through the analysis device, detecting means, and computational means for analyzing data and providing output.

In an embodiment of the third aspect the detecting means are imaging means.

In an embodiment of the third aspect the system comprises illuminating means for illuminating the immobilization zone of the reaction chamber.

Different non-binding aspects and embodiments of the present disclosure have been illustrated or will be illustrated.

The disclosed embodiments are used merely to explain selected aspects, embodiments or steps that may be utilized in implementations of the present disclosure. Some embodiments may be presented only with reference to certain example aspects of the present disclosure. It should be appreciated that corresponding embodiments may apply to other example aspects as well. Any appropriate combinations of the embodiments may be formed.

BRIEF DESCRIPTION OF THE DRAWINGS

The disclosed embodiments will now be described, by way of example only, with reference to the accompanying drawings, in which.

DETAILED DESCRIPTION

Definitions log P/log D refers to partition/distribution coefficient. It describes the lipophilic nature of the compound, determining the partition in e.g. the environment and the human body.

The pH independent partition coefficient P or the pH dependent distribution coefficient D describes e.g. permeation in biological membranes and absorption phenomena.

Figure 1:
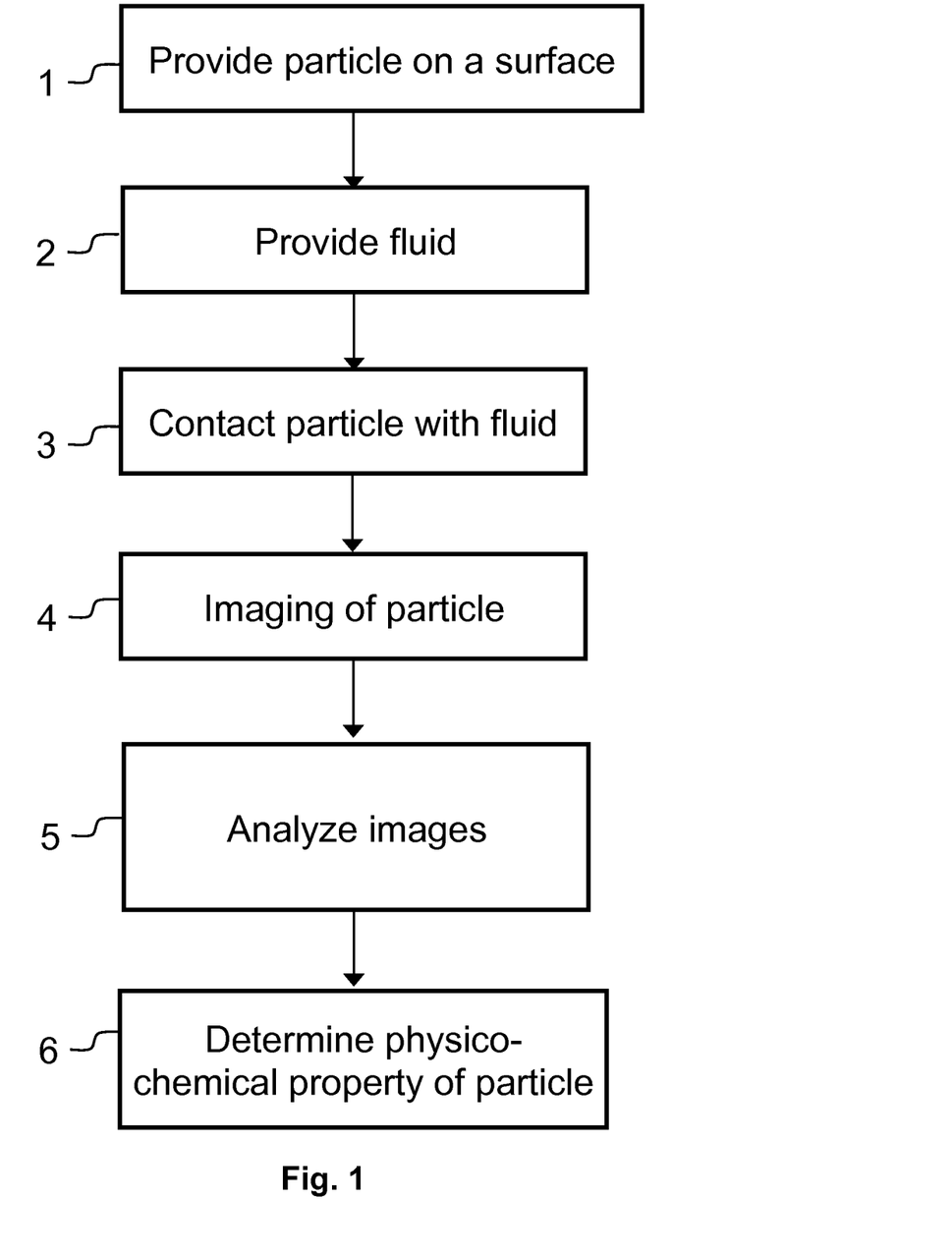
FIG. 1 shows a flow chart of a method in accordance with an example embodiment.

FIG. 1 shows as a schematic flow chart of the present method. First, at least one particle is provided on a surface, 1. A fluid is provided, 2, and contacted with the particle(s), 3. As the particle(s) is in contact with the fluid, the particle(s) is imaged, 4. The images acquired during detecting are analyzed, 4. After image analysis, at least one physicochemical property of the particle(s) is determined, 6, using the information obtained from the analyzed images.

As the particle(s) interacts with the fluid, e.g. dissolves when a solvent as a fluid dissolves the surface of the particle(s), the residual particle(s) is imaged sequentially in order to detect its size, shape, mass loss or gain, pressure difference, specific and non-specific adsorption, adhesion, reaction 4. The time-point of detecting or the time interval between the images may also be recorded. The change in shape and the size/mass loss or gain as a function of time is determined preferably using computerized image analysis means, 5. Finally, a physicochemical property of interest is determined using the information on the size, shape and/or mass loss or gain as a function of time.

In certain embodiments detecting changes may comprise detecting no change between two detection points.

In an embodiment the method is carried out using an analysis device according to the second aspect or the system according to the third aspect.

In an embodiment the particle(s) is immobilized in a stream formed by the fluid.

In an embodiment the particle(s) is immobilized on a permeable or semipermeable layer by fluid flow through the permeable or semipermeable layer.

In an embodiment the particle(s) is immobilized on the surface, and the surface is a permeable or semipermeable layer on which the particle(s) is immobilized by fluid flow through the permeable or the semipermeable layer.

In an embodiment the particle(s) is immobilized on a permeable/semipermeable layer by using a pressure difference of the fluid over the permeable/semipermeable layer.

The permeable/semipermeable layer may be arranged inside a reaction chamber through which the fluid flows such that substantially all of the fluid passes through the permeable/semipermeable layer.

In an embodiment the particle(s) is provided immobilized in an immobilization zone on an inner surface of the reaction chamber. In an embodiment immobilization is carried out by attaching the particle(s) on the surface e.g. by melting, by adhesion, by suction. In another embodiment the immobilization is arranged inside the reaction chamber by providing the particle(s) inside a membrane or an additional compartment.

In an embodiment the inner surface, or the surface on which the particle(s) is provided, is a permeable/semipermeable layer.

In an embodiment a semipermeable layer is used.

In an embodiment step iv. comprises detecting at least one part of the particle.

In an embodiment the particle is loaded using a fluid as a carrier. In an embodiment the fluid used as the carrier is an inert fluid.

In an embodiment more than one reaction chambers are used. The reaction chambers may be separate or integrated into one holder, e.g. wellplate wherein each well is a reaction chamber. The inlet and/or outlet flow may be controlled by separate pumps and devices or may be controlled by one device and divided into many fluid streams. Particles may be detected in the chambers using multiple detectors, using one moving detector or using one large detector for detecting all chambers simultaneously. This may increase the analysis throughput.

In an embodiment the permeable/semipermeable layer is a filter or a filter membrane, membrane or a porous layer. The permeable/semipermeable layer can be arranged such that the fluid flows through it, thereby immobilizing the particle(s) on the surface of the permeable/semipermeable layer and in the flowing fluid. In an embodiment the particle(s) is arranged between two porous layers, such as between membrane sheets.

In an embodiment the particle(s) is detected through a window in the reaction chamber. In an embodiment the particle(s) is immobilized on the surface, which is detected through the window.

In an embodiment detection is by using a probe or a detector arranged in the wall of the reaction chamber. In an embodiment the detector may be a CCD or CMOS sensor. In an embodiment the probe may be an optical fiber, or more than one optical fibers.

In an embodiment the particle(s) is loaded inside the reaction chamber using a fluid as a carrier. In an embodiment the particle(s) is loaded using the same inlet and the same fluid, which is used to analyze properties of the particle(s). In another embodiment the particle(s) is loaded using a different inlet and optionally a loading fluid, which may be the same or different compared to the fluid in which properties of the particle(s) are analyzed. The loading fluid may be in inert fluid.

In an embodiment the particle(s) is loaded manually, automatically, pre-loaded, or loaded mechanically using for example a micro manipulator.

In an embodiment the particle(s) is immobilized on the surface of the permeable/semipermeable layer by allowing flow of the fluid through the porous layer to immobilize the particle(s) during detecting.

In an embodiment the particle(s) is immobilized by suction. Suction may be achieved using the fluid stream and providing a pressure difference.

In an embodiment the fluid flow is laminar.

In an embodiment the fluid flow is turbulent.

In an embodiment the particle(s) are immobilized on a permeable/semipermeable surface and the density of the particle(s) is lower than that of the fluid, i.e. the particle(s) float in the fluid. Preferably in such a case the flow or device is reversed, i.e. the flow is from bottom to top to keep the particle(s) on the lower side of the porous layer. This is particularly advantageous when the fluid flow rate is low.

In another embodiment the fluid flow is horizontal. In such an embodiment the permeable/semipermeable layer is optionally vertical. A skilled person is able to modify the analysis device, including changing the position of the inlets and outlets accordingly to obtain a horizontal flow device.

In an embodiment the fluid is in a homogenous state inside the reaction chamber.

In an embodiment a gradient in a property of the fluid is provided inside the reaction chamber. For example a pH, pressure and/or temperature gradient may be created inside the reaction chamber. This may be achieved by using multiple flow inlets or by integrating a thermoelectric or fluid cooling/heating functionality in the device. In a further embodiment an electrical or magnetic field is applied over or inside the reaction chamber.

In an embodiment the particle(s) is a chemical, biochemical or biological particle(s), such as tissue, cell, virus, powder particle(s), crystal, pellet, gel, granule, grain, fiber, vesicle, liposome, polymersome, a polymeric structure, or a mixture thereof.

In an embodiment at least two particles are provided, and the particles are composed of the same material or chemical compound, or they are composed of at least two different materials or chemical compounds. Thus, a plurality of particles having different chemical composition can be provided on the surface and characterised.

In another embodiment the particle, or at least some of the plurality of particles, comprises more than one material or chemical compound. In another embodiment the particle is a mixture comprising more than one chemical compound, material or matter.

In an embodiment the fluid is transparent. In an embodiment transparency comprises transparency in the portion of the electromagnetic spectrum used for carrying out detecting. In an embodiment transparency comprises optical transparency.

In an embodiment the fluid is liquid, supercritical fluid, ionic fluid, gas, biological fluid, fluid containing bacterial flora, fluid containing a protein such as an enzyme, a flowing phase, a dispersion, or a mixture thereof.

In an embodiment the fluid is a supercritical fluid, and the method optionally further comprises controlling pressure. In another embodiment the physicochemical property is solubility.

In an embodiment the fluid is recycled during the method or in the device.

In an embodiment the fluid is not recycled during the method or in the device.

In an embodiment the detecting is carried out using optical detecting. In another embodiment detecting is by ultrasound detecting; by spectroscopy including UV, Raman and IR spectroscopy; interferometry, scanning electron microscopy (SEM), transmission electron microscopy (TEM), nuclear magnetic resonance (NMR) or any other suitable detecting means, in situ detection or a combination thereof. In one embodiment in situ detection comprises detecting within an enclosed chamber using a probe, such as a fiber optic probe, Raman probe, UV probe, IR probe or ultrasonic probe. In one embodiment in situ detection comprises detecting with a detector integrated into a structure, such as one or multiple walls of the chamber.

When ultrasound detecting is used, in an embodiment the ultrasound probe is provided in direct contact with the fluid in the reaction chamber. The probe may be integrated in the reaction chamber.

In an embodiment detecting comprises acquiring a sequence of images. The images may be acquired at predetermined intervals such as regular intervals. In an embodiment images are micrographs acquired using optical microscopy.

In an embodiment, when the detecting is carried out using ultrasound detecting the fluid is not optically transparent.

In an embodiment detecting is two-dimensional detecting. In an embodiment detecting is three-dimensional and/or two-dimensional detecting. In an embodiment three-dimensional detecting is performed using one or multiple detector by means of confocal microscopy, or by moving the one or more detectors or other part of the device. In an embodiment the three-dimensional detecting is performed using multiple integrated, in situ or external detectors. In an embodiment the three-dimensional detecting is performed using one integrated, in situ or external detector. In a further embodiment, the radiation is transferred to a detector via the means of one or multiple mirrors, prisms and/or lenses.

In an embodiment the particle(s) are illuminated. Suitable illuminating methods include collimated radiation, polarized radiation, polychromatic radiation, monochromatic radiation, coherent or incoherent radiation, or any combination thereof. In an embodiment the illumination is performed from one direction of choice. In on embodiment the illumination is performed from multiple directions at once. In one embodiment the illumination is performed from multiple directions in a predetermined or random sequence.

In an embodiment analyzing the images involves measuring at least one of radius, projection area, surface area, volume, intensity, colour, circumference, sphericity of the particle(s), or at least one part thereof.

In an embodiment the at least one part measured is a corner, edge, side, face, prominent and/or projecting part of the particle(s).

In an embodiment the physicochemical property comprises at least one of dissolution, morphological change, shrinking, expanding, growing, burning, oxidation, reduction, evaporation, sublimation, condensation, corroding, adsorption, absorption, desorption, resorption, binding, wetting, or any reverse process of the afore mentioned properties. In an embodiment the physicochemical property is the stability or non-change of the detected material. In an embodiment the detected property is directional, isotropic or anisotropic. In an embodiment the detected property is in all directions.

In a preferred embodiment the physicochemical property is solubility.

In another preferred embodiment the characterization method comprises correlating the changes to at least one physicochemical property of the material of the particle, and the physicochemical property is solubility.

In an embodiment a verification step is used to determine a time point when detecting is stopped and/or analysis is ready. In a preferred embodiment the verification step is verification using a proper method, such as a statistical method.

In an embodiment the particle(s) has an original mass not higher than 100 mg, preferably not higher than 100 µg, more preferably not higher than 500 ng, more preferably not higher than 100 ng.

In an embodiment the method is for determining ng, preferably pg, even more preferably fg, most preferably ag changes in the mass of the particle(s).

In an embodiment the method comprises analyzing the chemical composition of the fluid exiting the reaction chamber. Chemical analysis may comprise e.g. chromatographical analysis, spectroscopical analysis or mass analysis.

In an embodiment the method comprises creating a pressure difference over the porous layer. This may enhance the attachment of the particle(s) on the surface and improving flow through the porous layer. Further, this may improve keeping the flow in the top part of the reaction chamber laminar.

In an embodiment the temperature of the fluid and optionally the fluid in the reaction chamber is controlled.

In an embodiment the pH of the fluid and optionally the fluid in the reaction chamber is controlled.

In an embodiment the ionic strength of the fluid and optionally the fluid in the reaction chamber is controlled.

In an embodiment the composition of the fluid and optionally the fluid in the reaction chamber is controlled.

In an embodiment the composition of the fluid is achieved before entering the reaction chamber. In another embodiment the composition of the fluid is achieved inside the reaction chamber.

In an embodiment the pressure inside the reaction chamber and optionally throughout the device is controlled.

In an embodiment an electric field is provided over a region in the reaction chamber occupied by the fluid, and optionally a region wherein a particle(s) is provided.

In an embodiment a magnetic field is provided over a region in the reaction chamber occupied by the fluid, and optionally a region wherein a particle(s) is provided.

In an embodiment the fluid comprises an indicator such as a pH indicator, ionic strength indicator, a redox indicator, a fluorescent indicator or a complexometric indicator.

Figure 2:
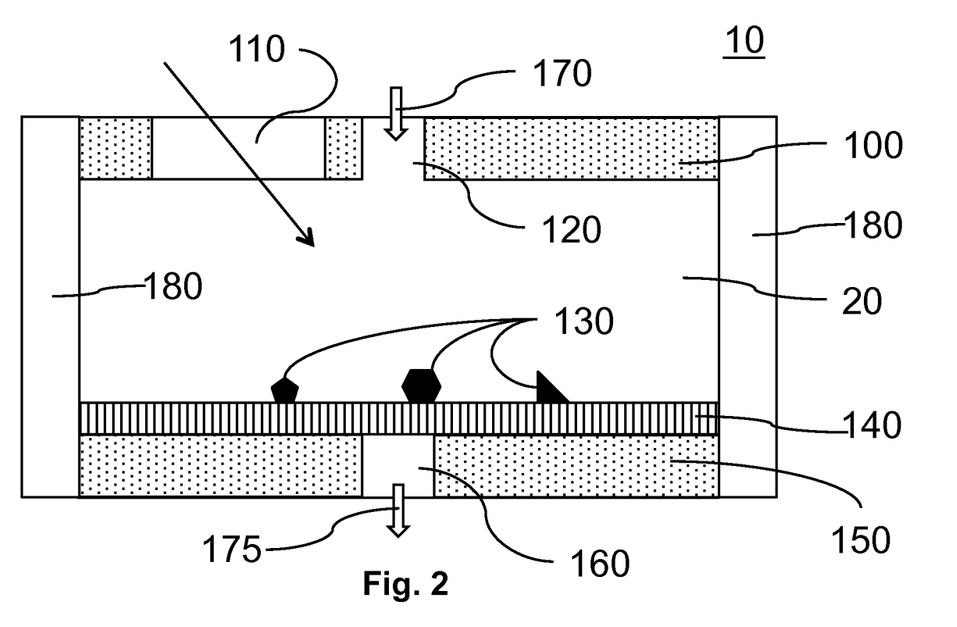
FIG. 2 shows a sectional view of an embodiment of the analysis device

FIG. 2 shows a schematic representation of an embodiment of the analysis device 10. The analysis device 10 comprises a reaction chamber 20, which is defined by wall 180, a top plate 100 and a bottom plate 150. The analysis device 10 comprises at least one first inlet 120 for passing fluid 170 into the reaction chamber 20, and at least one outlet 160 for passing fluid 175 outside the reaction chamber. Inside the reaction chamber is a permeable/semipermeable layer 140 arranged on the bottom plate, functioning as the immobilization zone in this embodiment. Particle(s) 130 to be imaged are arranged on the permeable/semipermeable layer 140. The at least one window 110 is arranged in the wall, top plate or bottom plate for allowing detecting the surface of the porous layer which faces the top plate. The particle(s) 130 can be imaged through the window 110.

The inlet 120 may receive the fluid from a fluid reservoir optionally connected to controlling means that provide fluid stream into the reaction chamber. The controlling means may comprise at least one of pump, mixer, heating element, cooling element, degassing means.

The reaction chamber 20 may be temperature controlled. This can be achieved by using heating or cooling elements integrated in the structure of the analysis device 10. Said elements can be provided in the top plate 100, bottom plate 150 and/or side walls 180 of the device, or they can be provided outside the analysis device 10. When temperature control is desired, material having good heat conductivity is preferably used to manufacture the analysis device 10.

The reaction chamber 20 may also be pressure controlled. When pressure above or below ambient pressure is used inside the chamber, the material of the analysis device is selected such that it does not restrict operation in the selected pressure.

The fluid 175 exiting the reaction analysis device 10 may be further analyzed. For example the chemical composition of the fluid 175 may be analyzed and compared with the composition of the fluid 170. Such analysis may be used to reveal substances dissolved or attached on the particle(s) 130, or changes the particle(s) is able to create in the fluid.

The analysis device 10 may also be provided with more than one window 110. In this embodiment the window 110 is the means allowing detecting the immobilization zone. When using more than one window it may be possible to image the particle(s) 130 from different view, and/or to use a different detecting method. A window may also be provided to carry out spectroscopy on the particle(s).

The analysis device 10 may also be enclosed without windows 110. In this case the detection of particle(s) 130 is performed with probes or integrated detectors.

The top plate 100 may be detachable from the analysis device 10 for loading and unloading particle(s) 130, and optionally the permeable/semipermeable layer 140. Alternatively, the bottom plate 150 may be detachable and it may be configured to be detachable with the porous layer 140. In this configuration loading and unloading of particle(s) 130 may be carried out by opening the bottom plate and exposing the permeable/semipermeable layer 140. The analysis device 10 may also be closed. In this case the loading of the particle(s) is performed through one of the inlet or outlet channels.

In an embodiment the permeable/semipermeable layer 140 is configured to receive at least one particle via a fluid stream.

In an embodiment the reaction chamber is cylindrical or substantially cylindrical.

In an embodiment the reaction chamber is rectangular or substantially rectangular.

In an embodiment the reaction chamber is shaped in a preferred geometric form, producing a fluid flow and/or gradient within the chamber.

In an embodiment the means allowing detecting the immobilization zone comprises a window. In another embodiment said means are integrated in the structure defining the reaction chamber, such as a top plate, a bottom plate or the wall of the reaction chamber. For example a probe can be integrated.

In an embodiment the means allowing detecting comprises a window arranged in a top plate or a bottom plate, or in a wall defining the reaction chamber. Optionally the top plate, bottom plate or the wall is detachable.

In an embodiment the top plate, the bottom plate or the wall is the window.

In an embodiment the window in arranged in a detachable top plate or a bottom plate.

In an embodiment the window is provided by arranging an opening, thereby providing an open system. The opening may partially open the reaction chamber, or it may extend to the wall of the reaction chamber thereby leaving open the whole top part of the reaction chamber. As an example embodiment, an open system can be made of analysis device 10 shown in FIG. 2 by providing the device without the top plate 100, or by providing an opening in the place of the window 110. In an embodiment the diameter of the inlet 170 may be increased sufficiently to allow detecting through the opening.

In an embodiment the means allowing detecting are integrated in the wall, top plate or bottom plate of the device.

In an embodiment of the analysis device the immobilization zone comprises a permeable/semipermeable layer configured to receive at least one particle via fluid stream.

In an embodiment detecting is 3D imaging and the reaction chamber is transparent for allowing detection from more than one view. Detecting may comprise using mirrors, prisms, or combinations thereof.

In an embodiment the top plate or the bottom plate is a lid for allowing loading a particle(s). In an embodiment the permeable/semipermeable layer is interchangeable and configured to be changed through the lid. In another embodiment the particle(s) is loaded inside the reaction chamber together with the porous layer.

In an embodiment the particle(s) is loaded inside the reaction chamber with a fluid flow. In an embodiment the particle(s) is manually loaded inside the reaction chamber with a suitable means such as a pin, needle, tweezer or micromanipulator. In an embodiment the particle(s) is automatically loaded inside the reaction chamber with a suitable means.

The analysis method or the system may be controlled by a control system. In an example embodiment, the analysis device is a component in a computer-controlled analysis system. A computer program stored into a memory of the system comprises instructions, which upon execution by at least one processor of the system cause the analysis system to operate as instructed. The instructions may be in the form of computer-readable program code.

Figure 3:
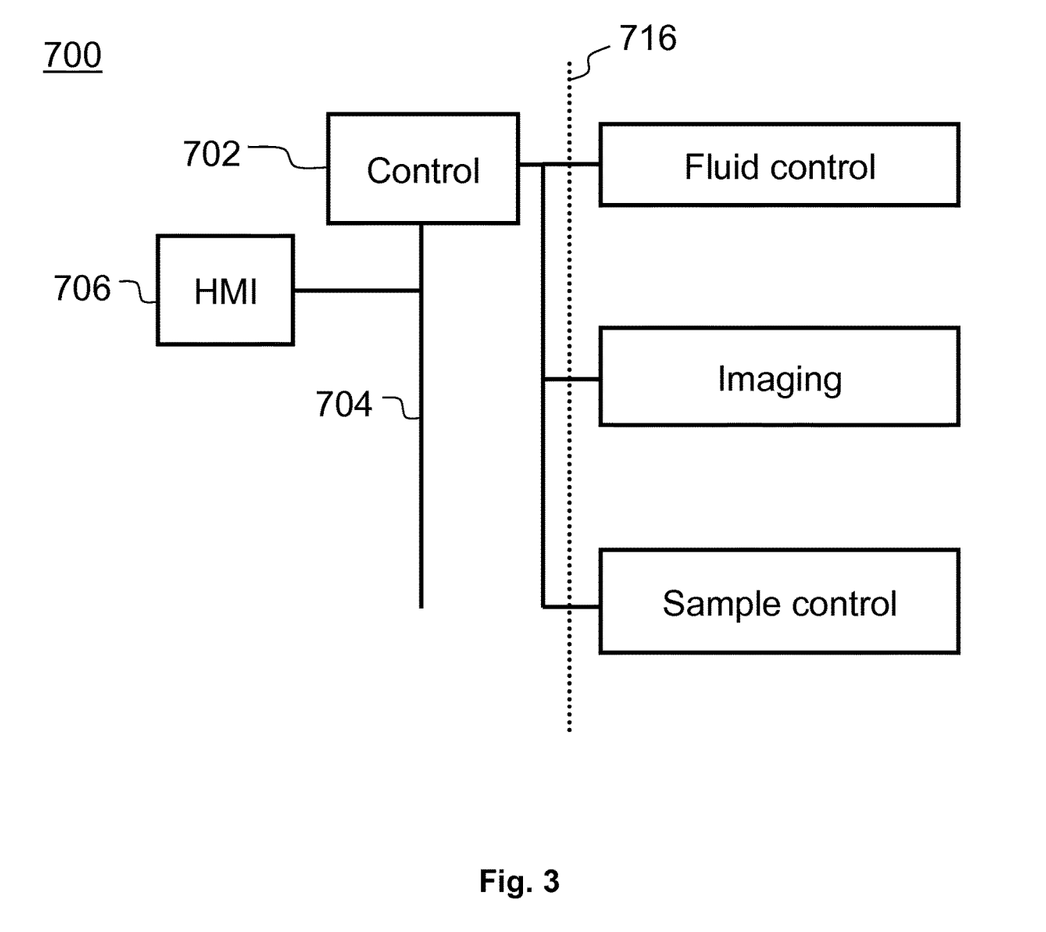
FIG. 3 shows an embodiment of a block diagram of an analysis control system

FIG. 3 shows a rough block diagram of an analysis control system 700. In a basic system setup process parameters are programmed with the aid of software and instructions are executed with a human machine interface (HMI) terminal 706 and downloaded via bus 704 to a control box 702. In an embodiment, the control box 702 comprises a general purpose programmable logic control (PLC) unit. The control box 702 comprises at least one microprocessor for executing control box software comprising program code stored in a memory, dynamic and static memories, I/O modules, A/D and D/A converters and power relays. The control box 702 sends electrical power to controllers of fluid line valves and pumps (not shown in FIG. 4) of the analysis system, and has two-way communication with in-feed fluid controllers (not shown in FIG. 4), and controls the operation of the fluid control and detecting, as well as otherwise controls the operation of the analysis system. The control box 702 may also control valves and pumps required when using multiple fluids. The control box 702 may measure and relay probe readings from the analysis system to the HMI terminal 706. The control box 702 may also control sample handling such as loading and unloading, or optional post-processing analysis of the fluid such as chromatography or mass analysis. A dotted line 716 indicates an interface line between the analysis system parts and the control box 702.

Detecting

The detecting can be carried out by any suitable technique capable of obtaining information on the deformation or stability of the particle(s), or any part thereof, as it changes or undergoes no change. Examples include imaging, optical microscopy (producing an image corresponding to the interaction of light with the particle(s)), fluorescence microscopy (producing an image corresponding to or signal proportional to fluorescent absorption or emission of the particle(s)/ substance upon suitable excitation), ultraviolet detecting (producing an image and/or a spectra corresponding to or signal proportional to ultraviolet light absorbed and/or emitted by the particle(s)/substance), Raman-spectroscopy (producing a spectra and/or an image based on Raman scattering of the particle(s)), infrared spectroscopy (producing an image and/or a spectra corresponding to or signal proportional to infrared radiation absorbed and/or emitted by the particle(s)/substance), interferometry (producing an image based on the interference pattern, produced by radiation interacting with the sample), diffraction and dynamic light scattering (giving data about the particle(s) size, determined by the diffraction and/or scattering of light).

The detecting techniques are as such known and can be directed to small volumes as required by the present invention to get information on the properties of at least one individual particle or at least one part thereof. Suitable detecting devices are commercially available. What needs to be taken care of is that the vessel wall or window therein is transparent to the radiation used by the detecting system. That is, the vessel itself must not significantly attenuate or alter the radiation to be recorded by the detecting device, for example optical wavelengths in the case of an optical microscopy.

In an embodiment the detector is calibrated. Calibration may be achieved by producing a calibration curve using compounds of known fluid, such as water, solubility at a constant temperature.

In an embodiment the calibration involves using crystal density data and/or molecular weight data.

The detecting may utilize direct illumination, backlight illumination, stroboscopic illumination, fluorescent, phosphorescent, or self-illumination of the sample.

Data Analysis

The images or any other detection data obtained from a detecting device may be stored on an analysis unit, such as a computer, where they are analyzed, using appropriate software and algorithms, in order to determine the physicochemical property, e.g. solubility, as desired. The images or any other detection data can also be stored on an external data storage connected to the system. The analysis depends on the detecting technique used, since the origin of the recorded radiation is different.

In the case of optical microscopy, each of the images obtained comprises a "micrograph", i.e. projection image, of the particle(s) at different stages of e.g. the dissolution process and potentially at different orientations. Different orientations of a particle(s) can be imaged e.g. using multiple detecting devices, mirrors, reflectors, using multiple light sources, multiple imaging devices, prisms.

In one embodiment, image processing comprises at least one of:
  determining sizes of the projection of the particle(s) residue, i.e., based on the cross-sectional surface areas thereof, from the successive images,
  determining shapes of the projection of the particle(s) residue, i.e., based on the cross-sectional surface areas thereof, from the successive images,
  estimating the relative or absolute mass of the particle(s) residue (or mass released from the particle(s) compared with the first image, or estimated initial particle(s) size) based on data from the cross-sectional surface areas,
  determining the dissolution rate based on the sizes of the particle(s) residues and information on detecting times,
  determining the intrinsic dissolution rate based on the sizes of the particle(s) residues, detecting times and surface area information extracted from the images,
  determining the solubility of a substance based on the sizes of the particle(s) residues and detecting times extracted from the images.
  determining the pKa and/or charge state of a substance based on the sizes of the particle(s) residues and detecting times extracted from the images.
  determining the partition (log P) and distribution (log D) coefficients of a substance based on the sizes of the particle(s) residues and detecting times extracted from the images.

According to one embodiment, computation of the desired physicochemical property or properties is carried out in real time as the detecting proceeds, based on the data obtained until that. The result may be an approximate in the beginning and accuracy is improved as more data becomes available. The data analysis may also be iterative and a 3D particle(s) reconstruction with topographical and morphological information derived from the image data.

According to another embodiment, the computation of the physicochemical property or properties is carried out only after the dissolution process has reached a predefined point, after which the process can be terminated.

Without limiting the scope and interpretation of the patent claims, certain technical effects of example embodiments disclosed herein are listed in the following: A technical effect is possibility for high-content screening of particle(s) and substances. Another technical effect is determining solubility of very poorly soluble substances. Another technical effect is non-invasive determination of physicochemical properties of matter, such as particles of matter. Another technical effect is possibility to use several fluids per one particle(s) or several particle(s) per one or more fluids.

EXAMPLES

The non-specific and wide applicability of the method is demonstrated by determining the dissolution rate and solubility of model compounds of diverse chemical structure and properties.

The applicant has used fourteen model compounds: acetaminophen
(Hawkins Inc., Minn., USA), bioactive glass S53P4 (BonAlive Biomaterials Ltd, Turku, Finland), celecoxib (Kemprotec, Carnforth, UK), dicalciumphosphate 2-hydrate (Chemische Fabrik Budenheim KG, Budenheim, Germany), furosemide (TCI Europe, Zwijndrecht, Belgium), hydrochlorothiazide (Alfa Aesar, Lancashire, UK), ibuprofen (Orion Pharma, Espoo, Finland), indomethacin (Hawkins, Minn., USA), insulin human recombinant (SAFC Pharma, Mo., USA), itraconazole (Orion Pharma, Espoo, Finland), ketoprofen (Orion Pharma, Espoo, Finland), naproxen (ICN Biomedichals Inc., Ohio, USA), phenytoin (Orion Pharma, Espoo, Finland), probenecid (Sigma-Aldrich Chemie Gmbh, Steinheim, Germany) for which solubility is of high relevance.

Indomethacin is a weak acid organic drug molecule, commonly used as a model compound for poorly soluble drugs. The water solubility of indomethacin is commonly presented as "practically insoluble". Such qualitative descriptors, while of little value, are often used as quantitation of very small amounts of analyte can be challenging. Further, only less than five percent of specifically trained computational models are able to accurately predict the solubility in simple aqueous buffer of studied compounds indomethacin and probenecid.

Insulin, in 1982, became the first introduced recombinant protein therapeutic. Early protein formulation approaches focused on decreasing the solubility of insulin, in order to achieve controlled and sustained release. Protein crystal engineering, e.g. cocrystallization, is still a widely used strategy in increasing the stability and effectivity of protein therapeutics. The rapid screening of physicochemical properties, such as dissolution rate and solubility, during the identification and optimization of such formulations requires reliable high-throughput methods.

Dicalcium phosphate dihydrate ($CaHPO_4 \cdot 2H_2O$, DCPD, brushite) is a biocompatible material clinically used in orthopedic and dental applications. It has also found applications in e.g. drug delivery, cancer therapy and in the development of biosensors. DCPD has a unique advantage over other calcium phosphate cement systems, through its ability to dissolve and be resorbed under physiological conditions. Over time DCPD is converted into the less soluble apatite mineral, depending on the immersion environment. The solubility and dissolution rate of such physiologically occurring minerals have a pathological relevance, determining for example the susceptibility to acid attack and remineralization of tooth enamel. The supersaturation of these minerals, determined by their solubility in various physiological environments, is also the driving force behind the formation of e.g. kidney stones.

Bioactive glass S53P4 is a FDA approved bone regeneration graft. Its bioactivity depends on the solubility, with the calcium and silicate ions released from the glass being known to promote the bone formation on the cellular level. Using the single crystal method the applicants were able to determine the aqueous solubility and dissolution rate of all model compounds at physiologically relevant conditions.

Additionally, the method was extended to determine a complete physicochemical profile (intrinsic solubility, native solubility, equilibrium solubility, dissolution rate, pKa, log P and log D) for the model drug indomethacin. A solubility-pH profile was performed in aqueous buffers over the physiologically relevant range of pH 2-9. Additionally the effective solubility was determined in three simulated body fluids (Fasted state simulated intestinal fluid (pH 6.5), fed state simulated intestinal fluid (pH 5) and fasted state simulated gastric fluid (pH 1.6) as well as two commonly used organic solvents (ethanol and octanol). It was observed that the solubility of the weak acid decreases linearly, starting from the highest pH 9, according to the decreasing degree of ionization, reaching a plateau after approximately pH 4.5. The pKa 4.4 for indomethacin was determined from the intersection of the two regression lines of the two phases of the solubility profile. As the aqueous solubility of the unionized form (S0, pH 2-3) as well as the solubility in octanol were acquired, the log P value of indomethacin was determined as 4.1. Additionally, using log P, pKa and pH data, the log D value was determined as a function of pH. All parameters determined using the present method correlated with theory and literature data. Thus, by only observing and characterizing one variable, i.e. the particle(s) size decrease of an individual crystal, it is possible to mine, in a high-content analysis (HCA) manner, a full physicochemical profile of six fundamental material characteristics for a material.

For real-time analysis a two-sample t-test analysis was applied on the slope of the linear regression line of two subsequent samples of ten. The slope was assumed to have reached a steady value when the p value of the t-test analysis decreased below 0.05. Using such a statistical verification, individual experiments can be terminated significantly earlier with sufficient degree of accuracy. At the real-time termination point, the slope differed on average 0.21 log units from the regression line slope of a full experiment. The uncertainty is within the RSD of the complete measurements and substantially less than the uncertainty of standard methods. We observed that the steady slope was reached generally within 0.4 minutes or after 20-30 data points, regardless of the studied substance. Therefore, rather than being substance dependent, the determination time seems to be controlled by the data acquisition speed and, thus, by the frame rate and resolution of the CCD sensor. This gives a strong indication that detecting based analysis of materials could be applied in high content screening (HCS) applications.

The average mass of the individual crystals analyzed was 5.0 ng. The substance needed for individual measurements using image based HCA may thus be more than three orders of magnitude less, than what is required in current state of the art miniaturized methods. The gain is much higher when comparing to standard methods, which operate in the mg and g scale. A full solubility-lipophilicity-charge state profile of model compound indomethacin could be obtained from the analysis of less than 400 ng of compound in total (n=69). This means that using HCA of individual crystals, the total amount analyzed for a full solubility-lipophilicity-charge state profile is above one order of magnitude less than the amount required for one experiment in one solvent using existing state of the art techniques. Moreover, the average change in mass between two subsequent detection points was 160 pg with a median of 5.4 pg and a minimum of 4.5 fg. At the real-time detection point of 0.4 minutes the average change in mass from the first data point was on average 5.8 ng with a median of 210 pg and a minimum of 180 fg. This sets the limit of quantitation of image analysis on the same level as that of current advanced analytical methods such as mass spectrometry. However, physicochemical characterization by HCA can be performed without any substance or solvent specific analytical method development. If necessary, the solubility in a specific chemical environment can be determined with adequate accuracy from the slope of the decreasing radius vector as the only required parameter. This means that a complete physicochemical profile can be determined for an unknown substance of unknown chemical and physical composition in any transparent solvent, within a minute. The simple and cost-effective setup, and the wide applicability using conventional optical microscopy, gives a substantial advantage to this technique.

The ability to screen physicochemical properties across a wide range of chemical environments is of great value in many fields. By using HCA, this is possible to achieve in an rapid, efficient, robust and cost-effective manner. We have shown that six fundamental physicochemical properties of matter, namely the dissolution rate, intrinsic solubility, solubility, pKa, log P and log D, can be determined from individual nanogram crystals using automated image analysis. Automated detecting based analysis of nanogram amounts of substance, without liquid sampling or sample treatment or handling steps, substantially reduces consumption and potentially toxic waste. In addition, operator contact with potentially hazardous substances is substantially reduced. It also allows for compounds of high value or scarce availability, such as in drug development, to be reliably analyzed.

Materials

Particle(s) Releasing Solutes

A total of 14 substances: acetaminophen (Hawkins Inc., Minn., USA), bioactive glass S53P4 (BonAlive Biomaterials Ltd, Turku, Finland), celecoxib (Kemprotec, Carnforth, UK), dicalciumphosphate 2-hydrate (Chemische Fabrik Budenheim KG, Budenheim, Germany), furosemide (TCI Europe, Zwijndrecht, Belgium), hydrochlorothiazide (Alfa Aesar, Lancashire, UK), ibuprofen (Orion Pharma, Espoo, Finland), indomethacin (Hawkins, Minn., USA), insulin human recombinant (SAFC Pharma, Mo., USA), itraconazole (Orion Pharma, Espoo, Finland), ketoprofen (Orion Pharma, Espoo, Finland), naproxen (ICN Biomedichals Inc., Ohio, USA), phenytoin (Orion Pharma, Espoo, Finland), probenecid (Sigma-Aldrich Chemie Gmbh, Steinheim, Germany) were analyzed in this work. The substances were chosen to represent a maximum variability in solubility and chemical properties.

Fluids as Solvents

Ultrapure deionized (MilliQ) water was used to dissolve 12 compounds of known aqueous solubility for producing the standard curve. Phosphate buffer solutions (pH 2.0, 3.0, 4.5, 5.8, 6.8, 8.0) and buffer solution (pH 9.0) were prepared according to the European Pharmacopoeia 8.8 chapter 4.1.3.1 Phosphate-buffered saline solution (Sigma-Aldrich, pH 7.4), as well as fed state simulated intestinal fluid (FeSSIF), fasted state simulated intestinal fluid (FaSSIF) and fasted state simulated gastric fluid (FaSSGF) were prepared according to the manufacturers' instructions. Ethanol (Altia, Rajamaki, Finland) and octanol (YA Kemia, Helsinki, Finland) were used as model organic solvents.

Analysis Device and Experimental Setup

Analysis device was constructed as a flow-through device consisting of two resistant flat metal plates. In the lower thereof a 1 mm hole was drilled as an outlet channel. The top metal plate hosted the inlet channel and was prepared with a glass window to facilitate detecting. A 0.2 µm inorganic membrane filter (Whatman nuclepore) was placed on the bottom plate and the particle(s) to be analyzed placed on top of the portion of the membrane filter being above the outlet channel. The two metal plates were tightly sealed before the start of an experiment. Solvents used as the fluids were degassed and pumped (Agilent 1260 Infinity Quaternary Pump) with a constant flow rate of 1 ml/min through the flow-chamber during all experiments. The temperature was adjusted by flowing the liquid through a thermostatted column compartment (Agilent 1200 Series). Particle(s) were imaged through the window with a 8MP CMOS image sensor (Gigastone, Calif., USA) on a Leica DMLB microscope mounted with a Leica 50× (N Plan L50×/0.50-∞/0/C) objective.

Determination of Physicochemical Factors

Solubility

Equilibrium solubility, S was calculated from image analysis data based on a reorganized single-particle diffusion layer model dissolution rate equation, $$S = \frac{\rho h(w_0^{1/3} - w_t^{1/3})}{\left(\frac{4\pi\rho}{3}\right)^{1/3} Dt}$$

where ρ is the density of the particle and h is the diffusion layer thickness, $w_0$ is the initial weight of the particle, $w_t$ is the weight of the particle at time t and D is the diffusion coefficient. Crystal weight was calculated based on molecular weight of a compound and true density of the crystal, using a spheroid approximation for the crystal volume. D was approximated from a simplified version of the Stokes-Einstein equation, $$D = \frac{2.40 \times 10^{-3}}{MW^{1/3}}$$

where MW is the molecular weight of the substance and h was estimated to 30 µm. The crystal density for all organic and inorganic compounds were acquired from literature, whereas the crystal density of recombinant human insulin was acquired as the inverse of the partial specific volume of the protein monomer.

To produce the calibration curve the equilibrium solubility value, in addition to the decreasing slope of the particle projection area and radius, were compared with equilibrium solubility values from literature. The projection area was directly acquired from pixel data and the radius was calculated based on equivalent circle approximation.

The pKa of model drug indomethacin was acquired from the intersection of the average intrinsic solubility value (pH 2 and pH 3) and the linear fit of the effective solubility of the ionized form (FIG. 2, Supplementary Tables 4 and 5). Based on pKa and pH data, the theoretical pH-dependent solubility function was calculated according to, $$S = S_0(10^{-pKa+pH} + 1)$$

where $S_0$ is the intrinsic solubility of the unionized form. Further, based on intrinsic solubility data in octanol and water the partition coefficient (log P) was determined according to, $$\log P_{oct/wat} = \frac{[HA_{oct}]}{[HA_{wat}]} = \frac{S_{oct}}{S_0}$$

and the distribution coefficient (log D) was estimated based on log P, pH and pKa values according to, $$\log D_{oct/wat} = \log P + \log\left[\frac{1}{1 + 10^{pH-pK_a}}\right]$$

Intrinsic dissolution rate can be determined based on surface area estimation and dissolution rate of the particle(s).

The foregoing description has provided by way of non-limiting examples of particular implementations and embodiments of the present disclosure a full and informative description of the best mode presently contemplated by the inventors for carrying out the invention. It is however clear to a person skilled in the art that the present disclosure is not restricted to details of the embodiments presented above, but that it can be implemented in other embodiments using equivalent means without deviating from the characteristics of the present disclosure.

Furthermore, some of the features of the above-disclosed embodiments of this present disclosure may be used to advantage without the corresponding use of other features. As such, the foregoing description should be considered as merely illustrative of the principles of the present disclosure, and not in limitation thereof. Hence, the scope of the disclosure is only restricted by the appended patent claims.

The invention claimed is:

1. A characterization method, comprising:
   i. providing at least one particle on a surface wherein the at least one particle is attached or immobilized on the surface;
   ii. providing at least one fluid;
   iii. allowing the at least one fluid to come into contact with the at least one particle;
   iv. detecting the at least one particle while attached or immobilized on the surface;
   v. analyzing from data acquired during the detecting changes in the at least one particle; and
   vi. correlating the changes to at least one physicochemical property of the at least one particle;
   wherein the surface is a permeable or semipermeable layer on which the at least one particle is attached or immobilized by fluid flow through the permeable or the semipermeable layer.

2. The method of claim 1, wherein the at least one particle is immobilized on the permeable or semipermeable layer by using a pressure difference of the at least one fluid over the permeable or semipermeable layer.

3. The method of claim 1, wherein step iv. comprises detecting at least one part of the at least one particle.

4. The method of claim 1, wherein the at least one particle has an original mass not higher than 100 mg.

5. The method of claim 1 for determining ng changes in mass of the at least one particle.

6. The method of claim 1, wherein the at least one particle is loaded on the surface using the at least one fluid as a carrier.

7. The method of claim 1, wherein the at least one particle is illuminated in iv.

8. The method of claim 1, wherein the at least one particle is detected through a window in reaction chamber comprising the at least one particle, the at least one fluid, and the surface.

9. The method of claim 1, wherein detecting comprises detecting no change between two data points.

10. The method of claim 1, wherein the at least one fluid is a supercritical fluid.

11. The method of claim 1, wherein the at least one physicochemical property is solubility.

12. A characterization method, comprising:
    i. providing at least one particle on a surface wherein the at least one particle is attached or immobilized on the surface;
    ii. providing at least one fluid;
    iii. allowing the at least one fluid to come into contact with the at least one particle;
    iv. detecting the at least one particle while attached or immobilized on the surface;
    v. analyzing from data acquired during the detecting changes in the at least one particle; and
    vi. correlating the changes to at least one physicochemical property of the at least one fluid;
    wherein the surface is a permeable or semipermeable layer on which the at least one particle is attached or immobilized by fluid flow through the permeable or the semipermeable layer.

* * * * *